(12) United States Patent
Kim et al.

(10) Patent No.: US 10,582,865 B2
(45) Date of Patent: Mar. 10, 2020

(54) NEURAL ELECTRODE FOR MEASURING NEURAL SIGNAL AND METHOD FOR MANUFACTURING THE SAME

(71) Applicant: ELECTRONICS AND TELECOMMUNICATIONS RESEARCH INSTITUTE, Daejeon (KR)

(72) Inventors: Yong Hee Kim, Daejeon (KR); Sang Don Jung, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 0 days.

(21) Appl. No.: 16/116,810

(22) Filed: Aug. 29, 2018

(65) Prior Publication Data

US 2019/0076038 A1    Mar. 14, 2019

(30) Foreign Application Priority Data

Sep. 14, 2017 (KR) .......................... 10-2017-0118059

(51) Int. Cl.
| | | |
|---|---|---|
| *A61B 5/04* | (2006.01) | |
| *C25D 9/04* | (2006.01) | |
| *C25D 5/34* | (2006.01) | |
| *C25D 7/06* | (2006.01) | |
| *B82Y 40/00* | (2011.01) | |
| *B82Y 30/00* | (2011.01) | |

(52) U.S. Cl.
CPC .......... *A61B 5/04001* (2013.01); *B82Y 30/00* (2013.01); *B82Y 40/00* (2013.01); *C25D 5/34* (2013.01); *C25D 7/0607* (2013.01); *C25D 9/04* (2013.01); *A61B 2562/125* (2013.01)

(58) Field of Classification Search
CPC ..................... A61B 5/04001; A61B 2562/125; C25D 9/04; C25D 7/0607; C25D 5/34; B82Y 40/00; B82Y 30/00
See application file for complete search history.

(56) References Cited

U.S. PATENT DOCUMENTS

| | | | |
|---|---|---|---|
| 7,905,013 B2 * | 3/2011 | Zhang | ............... A61N 1/0543 29/831 |
| 9,381,355 B2 | 7/2016 | Khraiche et al. | |
| 9,530,963 B2 | 12/2016 | Lim et al. | |

(Continued)

FOREIGN PATENT DOCUMENTS

KR    20100058220 A    6/2010

OTHER PUBLICATIONS

Muhammed K. Gheith et al., "Single-Walled Carbon Nanotube Polyelectrolyte Multilayers and Freestanding Films as a Biocompatible Platform for Neuroprosthetic Implants", Advanced Materials, Sep. 29, 2005, pp. 2663-2670, vol. 17.

(Continued)

*Primary Examiner* — Savitri Mulpuri (57) ABSTRACT

Provided are a neural electrode for measuring a neural signal, and a method for manufacturing the same. The method for manufacturing the same includes forming an ITO electrode on a substrate, forming a passivation layer for exposing a portion of the ITO electrode, forming ITO nanowires on the ITO electrode, and forming a metal oxide on the ITO nanowires.

10 Claims, 7 Drawing Sheets

(56) References Cited

U.S. PATENT DOCUMENTS

| | | | | |
|---|---|---|---|---|
| 10,270,004 | B2* | 4/2019 | Kim | G06F 3/041 |
| 10,365,750 | B2* | 7/2019 | Iwata | G06F 3/0416 |
| 2007/0194467 | A1* | 8/2007 | Yang | H01G 9/2027 |
| | | | | 257/784 |
| 2010/0127206 | A1 | 5/2010 | Choi et al. | |
| 2012/0199189 | A1* | 8/2012 | Jin | H01G 9/2031 |
| | | | | 136/256 |
| 2015/0277616 | A1* | 10/2015 | Wang | G06F 3/044 |
| | | | | 345/174 |
| 2016/0225631 | A1 | 8/2016 | Jun et al. | |
| 2016/0282978 | A1* | 9/2016 | Wang | G06F 3/044 |
| 2016/0340792 | A1* | 11/2016 | Moffat | C25D 5/18 |
| 2019/0157588 | A1* | 5/2019 | Kim | G02B 5/0242 |
| 2019/0161868 | A1* | 5/2019 | Jang | C25B 11/0447 |

OTHER PUBLICATIONS

Hoo Keun Park et al., "Fabrication and characterization of large-scale multifunctional transparent ITO nanorod films", Journal of Materials Chemistry A, Mar. 1, 2013, pp. 5860-5867, vol. 1, The Royal Society of Chemistry.

Jae Hyoung Park et al., "Wafer-Scale Growth of ITO Nanorods by Radio Frequency Magnetron Sputtering Deposition", Journal of The Electrochemical Society, Mar. 21, 2011, pp. K131-K135, vol. 158, No. 5, The Electrochemical Society.

Ilhwan Ryu et al., "Coaxial RuO2-ITO Nanopillars for Transparent Supercapacitor Application", Langmuir, 2014, pp. 1704-1709, vol. 30, American Chemical Society.

* cited by examiner

NEURAL ELECTRODE FOR MEASURING NEURAL SIGNAL AND METHOD FOR MANUFACTURING THE SAME

CROSS-REFERENCE TO RELATED APPLICATIONS

This U.S. non-provisional patent application claims priority under 35 U.S.C. § 119 of Korean Patent Application No. 10-2017-0118059, filed on Sep. 14, 2017, the entire contents of which are hereby incorporated by reference.

BACKGROUND

The present disclosure herein relates to a neural electrode for measuring a neural signal and a method for manufacturing the same.

Research has been conducted on the development of materials for improving the performance of neural electrodes in the field of in vivo or in vitro neural interface applications for the purpose of recording neural signals from neurons.

As for neural electrodes, from first-generation electrodes made of a metal wire, such as platinum, gold, tungsten, and iridium to second-generation electrodes made of a semiconductor or multiple arrays, and now third-generation electrodes which have been surface-modified with a nanostructure is being researched and developed as neural electrodes.

In order to assess the state of a nerve more accurately, recording a neural signal per each neuron is essential. To this end, the size of an electrode has been reduced to the size of a neuron (about 10 μm).

In order to maintain effective signal measurement sensitivity while maintaining a small size of a neural electrode, surface area per unit area must be large. To this end, surface modification using nano materials and the like has been attempted.

An increase in surface area may reduce thermal noise through a reduction in impedance, and ultimately may improve a signal-to-noise ratio (SNR).

Meanwhile, in the case of a neural electrode, since the affinity with neurons is very important, not only the nerve affinity of the neural electrode but also the nerve affinity of a neural electrode passivation material is also very important.

SUMMARY

The present disclosure provide a neural electrode for measuring a neural signal, the electrode capable of reducing impedance and increasing charge storage capacity, and a method for manufacturing the same.

An embodiment of the inventive concept provides a method for manufacturing a neural electrode including forming an ITO electrode on a substrate, forming a passivation layer for exposing a portion of the ITO electrode, forming ITO nanowires on the ITO electrode, and forming a metal oxide on the ITO nanowires.

In an embodiment, the metal oxide may include iridium oxide.

In an embodiment, forming the metal oxide may include electrodepositing the metal oxide on the ITO nanowires.

In an embodiment, electrodepositing the metal oxide may include preparing an iridium oxide sol, and electrodepositing the iridium oxide by providing the substrate in the iridium oxide sol.

In an embodiment, preparing the iridium oxide sol may include mixing iridium chloride with water.

In an embodiment, the method for manufacturing a neural electrode may further include adding hydrogen peroxide to the water, adding oxalic acid to the water, and adding a pH adjusting agent to the water.

In an embodiment, the pH adjusting agent may include potassium carbonate.

In an embodiment, electrodepositing the iridium oxide may include a CV method.

In an embodiment, the metal oxide may be formed to have a thickness less than half the distance between the ITO nanowires.

In an embodiment, the passivation layer may include silicon oxide.

In an embodiment, the substrate may include transparent glass.

In an embodiment of the inventive concept, a neural electrode includes an ITO electrode on a substrate, a passivation layer for covering edges of both sides of the ITO electrode, ITO nanowires on the ITO electrode which is exposed by the passivation layer, and a metal oxide disposed on the ITO nanowires to increase the surface area of the ITO nanowires.

In an embodiment, the metal oxide may include iridium oxide.

In an embodiment, the metal oxide may have a thickness less than half the distance between the ITO nanowires.

In an embodiment, the passivation layer may include silicon oxide.

In an embodiment, the substrate may include a transparent glass.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Hereinafter, preferred embodiments of the inventive concept will be described in detail with reference to the accompanying drawings. Advantages and features of the present inventive concept and methods of accomplishing the same may be understood more readily by reference to the following detailed description of exemplary embodiments and the accompanying drawings. However, the present inventive concept will be embodied in many different forms and is not limited to the embodiments set forth herein, Rather, these embodiments are also to complete the disclosure of the present inventive concept, ordinary skill in the art is provided for the fully convey the concept of the inventive concept to those, the present inventive concept will only be defined by the appended claims. The same reference numerals refer to like elements throughout the specification.

The terminology used herein is for the purpose of describing embodiments and is not intended to be limiting of the inventive concept. In the present specification, terms of a singular form may include terms of a plural form unless the context clearly indicates otherwise. As used herein, the terms "comprises" and/or "comprising" are intended to be inclusive of the stated elements, steps, operations and/or devices, and do not exclude the possibility of the presence or the addition of one or more other elements, steps, operations, and/or devices. In addition, since they are in accordance with the preferred embodiments, the reference numerals shown in the order of description are not necessarily limited to the order. Furthermore, in the present specification, it will also be understood that when a layer is referred to as being 'on' another layer or substrate, it can be directly on the other layer or substrate, or intervening layers may also be present.

In addition, embodiments described herein are described with reference to an ideal schematic plan view and a cross-sectional view of the present inventive concept. Therefore, manufacturing techniques and/or tolerances in the form of an illustration or the like may be modified. Thus, embodiments of the present inventive concept are not limited to the specific form shown, but also include changes in the form produced according to the manufacturing process. Accordingly, the areas illustrated in the drawings have schematic properties, and the shapes of the areas illustrated in the drawings are intended to illustrate a particular form of the area of the device and are not intended to limit the scope of the inventive concept.

Figure 1:
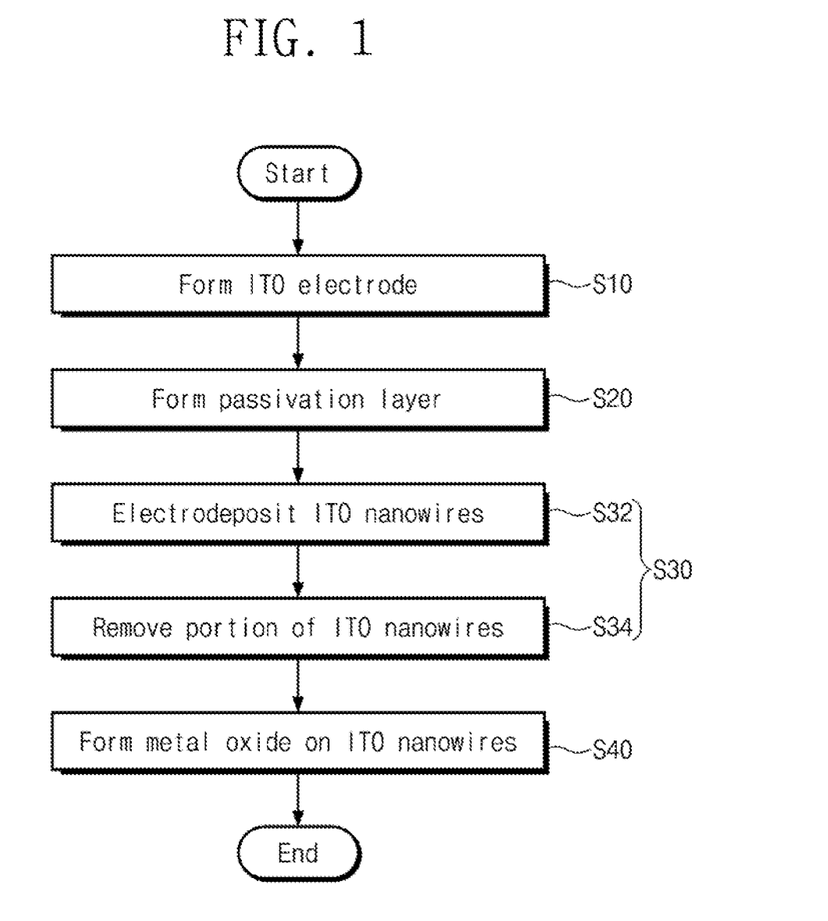
FIG. 1 is a flow chart showing a method for manufacturing a neural electrode for measuring a neural signal according to an embodiment of the inventive concept.

FIG. 1 is a flow chart showing a method for manufacturing a neural electrode for measuring a neural signal according to an embodiment of the inventive concept. FIG. 2 to FIG. 9 are process-sectional views showing a method for manufacturing a neural electrode for measuring a neural signal.

Referring to FIG. 1, a method for manufacturing a neural electrode for measuring a neural signal may include forming an ITO electrode on a substrate (S10), forming a passivation layer on edges of both sides of the ITO electrode (S20), forming ITO nanowires in the center of the ITO electrode (S30), and forming a metal oxide on the ITO nanowires (S40).

Figure 2:
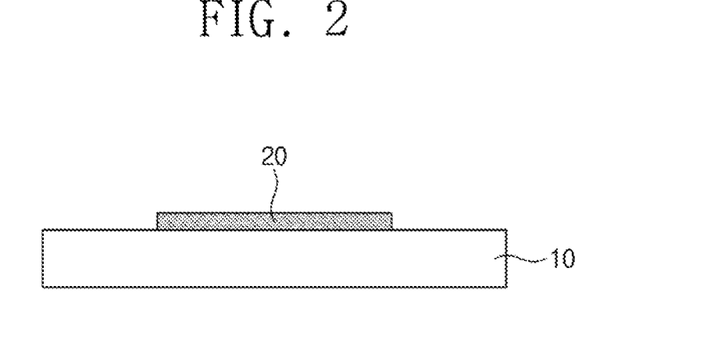
FIG. 2 to FIG. 9 are process-sectional views showing a method for manufacturing a neural electrode for measuring a neural signal.

Referring to FIG. 1 and FIG. 2, an ITO electrode 20 is formed on a substrate 10 (S10). The substrate 10 may include transparent glass or transparent quartz. Alternatively, the substrate 10 may include transparent plastic. The ITO electrode 20 may be formed by a sputtering method, a photolithography method, and an etching method.

Figure 3:
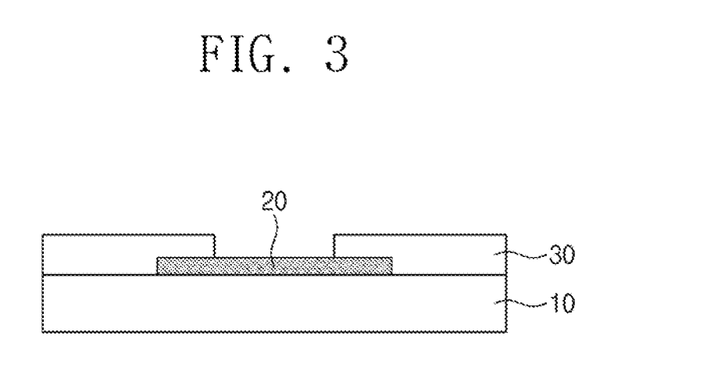

Referring to FIG. 1 and FIG. 3, a passivation layer 30 is formed on edges of both sides of the ITO electrode 20 (S20). The passivation layer 30 may include an insulator made of a silicon oxide film. The passivation layer 30 may be formed by a chemical vapor deposition method and an etching method.

Referring to FIG. 1, and FIG. 4 to FIG. 8, ITO nanowires 40 are formed in the center of the ITO electrode 20 (S30).

Forming the ITO nanowires 40 (S30) may include depositing the ITO nanowires 40 (S32) and removing a portion of the ITO nanowires 40 (S34).

Figure 4:
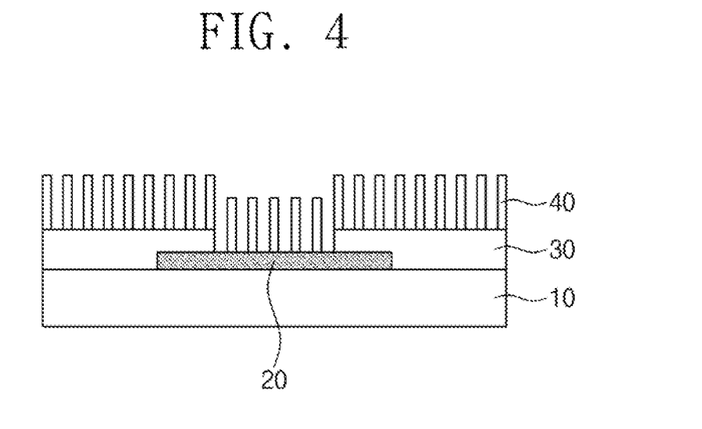

Referring to FIG. 1 and FIG. 4, the ITO nanowires 40 are deposited on the ITO electrode 20 and the passivation layer 30 (S40). The ITO nanowires 40 may be deposited by a sputtering method or a pulsed laser deposition (PLD) method. The ITO nanowires 40 have a whisker shape, and may be formed in a direction perpendicular to the substrate 10. The ITO nanowires 40 may have a height and/or length of about 2 μm to about 20 μm. The distance between the ITO nanowires 40 may be less than the height and/or length thereof.

Referring to FIG. 1, and FIG. 5 to FIG. 8, a portion of the ITO nanowires 40 are removed (S34). For example, the ITO nanowires 40 may be removed from the passivation layer 30 through a photolithography method and an etching method.

Figure 5:
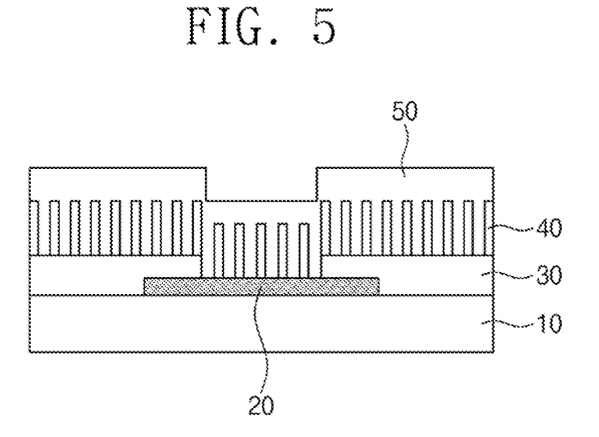

Referring to FIG. 5, a photoresist 50 is applied on the ITO nanowires 40. The photoresist 50 may be entirely applied on the top surface of the substrate 10 by a spin coating method.

Figure 6:
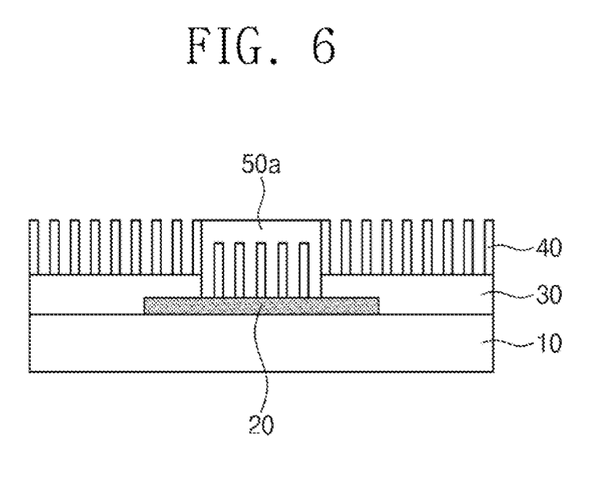

Referring to FIG. 6, a photoresist pattern 50a is formed by removing a portion of the photoresist 50. The photoresist 50 may be removed from the passivation layer 30. When the photoresist 50 is a positive photoresist, ultraviolet light may be selectively provided to the photoresist 50 on the passivation layer 30 through an exposure apparatus (not shown). Thereafter, the photoresist 50 may be developed by a developer. A portion of the photoresist 50 is removed from the passivation layer 30, and the photoresist pattern 50a may be formed on the ITO electrode 20.

Figure 7:
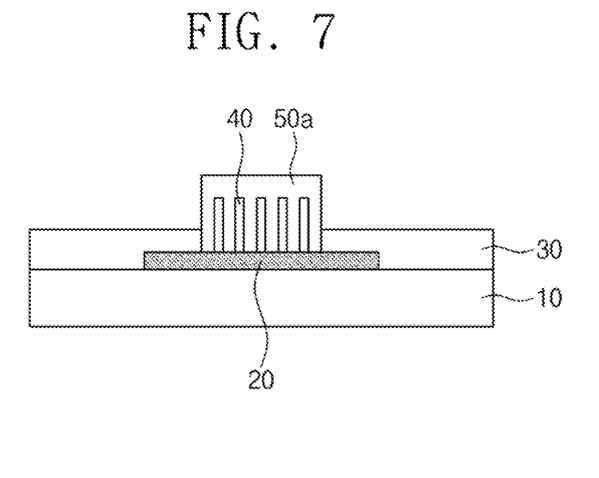

Referring to FIG. 7, the ITO nanowires 40 are removed from the passivation layer 30. When the ITO nanowires 40 are removed from the passivation layer 30, the photoresist pattern 50a may be used as an etching mask.

Figure 8:
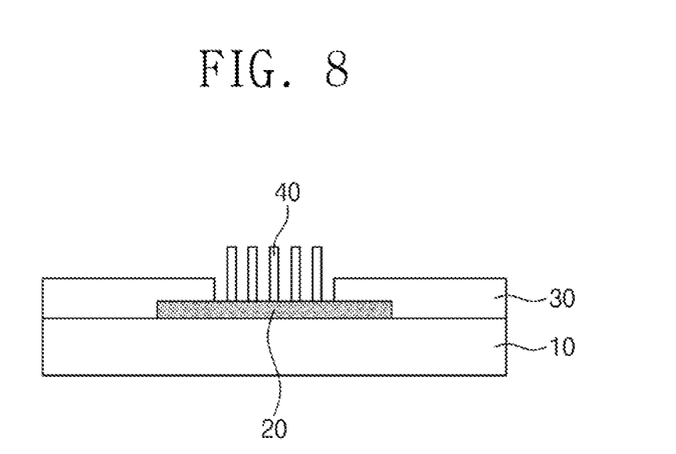

Referring to FIG. 8, the photoresist pattern 50a is removed. The ITO nanowires 40 may be formed on the ITO electrode 20 (S30). The photoresist pattern 50a may be removed using an organic solvent such as alcohol or acetone. The ITO nanowires 40 may be higher than the passivation layer 30.

Figure 9:
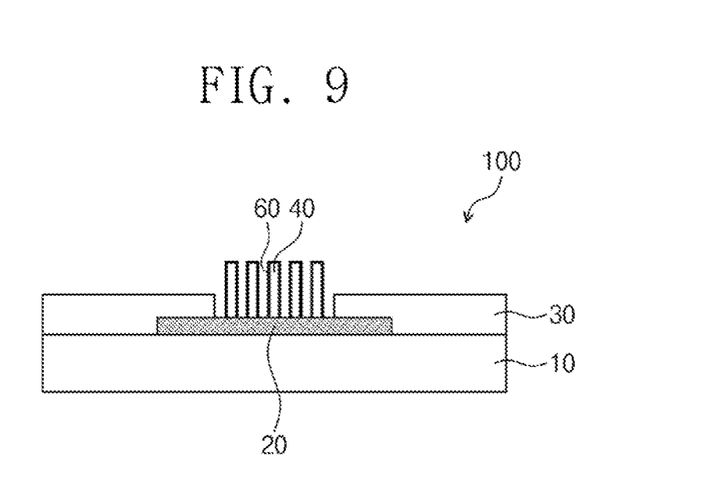

Referring to FIG. 1 and FIG. 9, a metal oxide 60 is formed on the ITO nanowires 40. According to an embodiment, the metal oxide 60 may include a rare earth metal oxide of iridium oxide. For example, the metal oxide 60 may be formed by an electrodeposition method.

Figure 10:
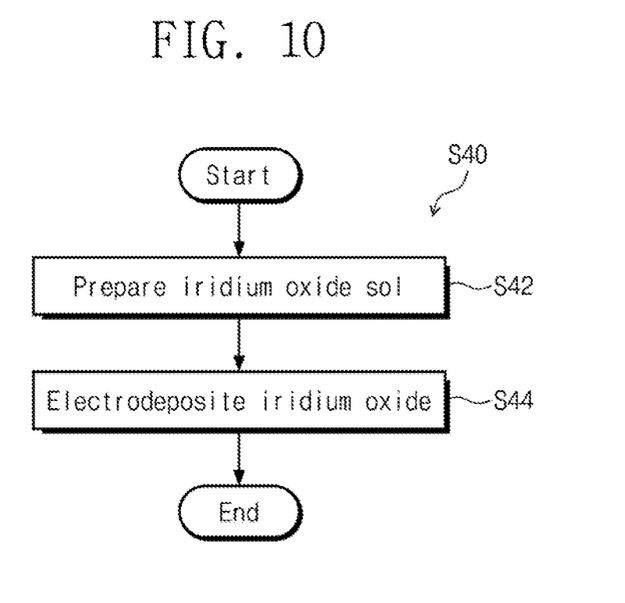
FIG. 10 is a flow chart showing one example of forming a metal oxide on the ITO nanowires of FIG. 1.

FIG. 10 shows one example of forming the metal oxide 60 on the ITO nanowires 40 (S40) shown in FIG. 1.

Referring to FIG. 10, forming the metal oxide 60 (S40) may include preparing an iridium oxide sol (S42), and electrodepositing the metal oxide 60 on the ITO nanowires 40 (S44).

Figure 11:
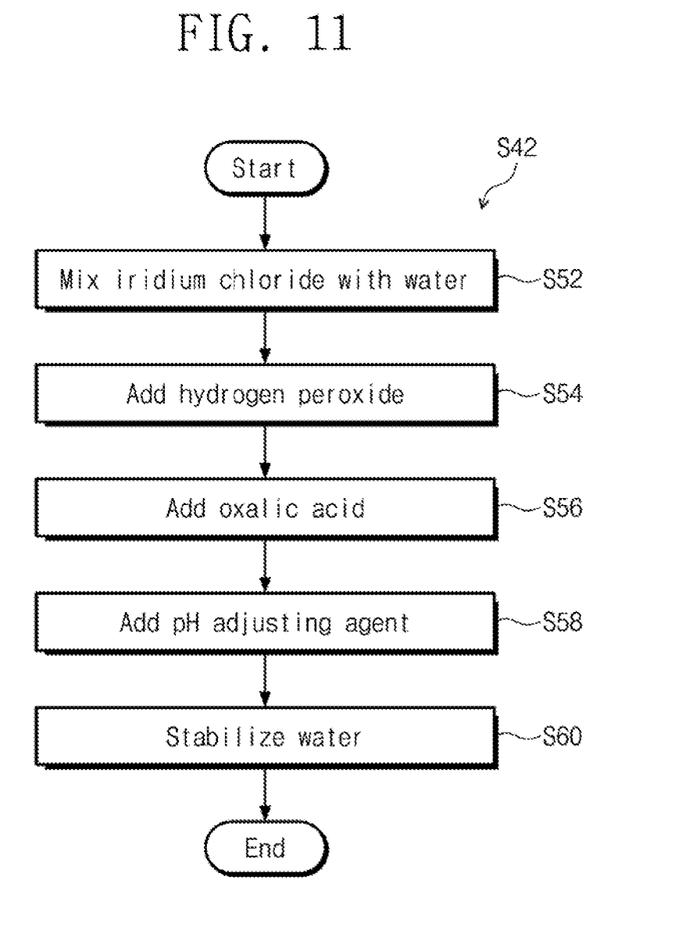
FIG. 11 is a flow chart showing one example of preparing the iridium oxide sol of FIG. 10.

FIG. 11 shows one example of preparing the iridium oxide sol (S42) shown in FIG. 10.

Referring to FIG. 11, preparing the iridium oxide sol (S42) may be preparing an electrodeposition solution of the metal oxide 60. According to an embodiment, preparing the iridium oxide sol (S42) may include mixing iridium chloride with water (S52), adding hydrogen peroxide (S54), adding oxalic acid (S56), adding a pH adjusting agent (S58), and stabilizing the water (S60).

First, about 0.07 g of the iridium chloride is mixed with about 50 ml of the water (S52). The water and the iridium chloride may be mixed and/or stirred for about 30 minutes.

Next, the hydrogen peroxide diluted to about 30% and having a volume of about 0.5 ml is added to the water (S54). The water and the hydrogen peroxide may be mixed and/or stirred for about 5 minutes.

Thereafter, about 250 ml of oxalic acid is added to the water (S56). The water and the oxalic acid may be mixed and/or stirred for about 10 minutes.

Thereafter, a pH adjusting agent is added to the water (S58). The pH of the water may be set to about 10.5. The pH adjusting agent may include potassium carbonate.

Then, the water is stabilized at room temperature (ex, about 20° C.) for a predetermined period of time (ex, about 10 hours or more) (S60) to produce the iridium oxide sol. The water may have a purple color.

Referring back to FIG. 9 and FIG. 10, the substrate 10 is provided in the iridium oxide sol to electrodeposit the metal oxide 60 on the ITO nanowires 40 (S40). The metal oxide 60 may be formed by a cyclic voltammetry method. The metal oxide 60 may be formed at a rate of about 100 mV/sec in a voltage range of about −0.05 V to about 0.8 V. The inventive concept is not limited thereto, and the metal oxide 60 may be formed by various methods.

The metal oxide 60 may have higher adhesion to the ITO nanowires 40 and/or the ITO electrode 20 than a metal. This is because the ITO nanowires 40 and/or the ITO electrode 20 are oxides of the same kind as the metal oxide 60.

The metal oxide 60 may increase surface area of a neural electrode 100 to reduce impedance thereof, and may increase charge storage capacity. When the thickness of the metal oxide 60 increases, the surface area of the metal oxide 60 may increase. According to an embodiment, the metal oxide 60 may be formed to a thickness less than half the distance between of the ITO nanowires 40. For example, when the thickness of the metal oxide 60 is greater than half the distance between the ITO nanowires 40, the metal oxide 60 may connect the ITO nanowires 40 to reduce the surface area of the neural electrode 100. For example, when the length or distance of the ITO nanowires 40 is about 2 μm to about 20 the metal oxide 60 may have a thickness of about 1 μm or less. The metal oxide 60 may be formed to a thickness of about 5 nm.

Figure 12:
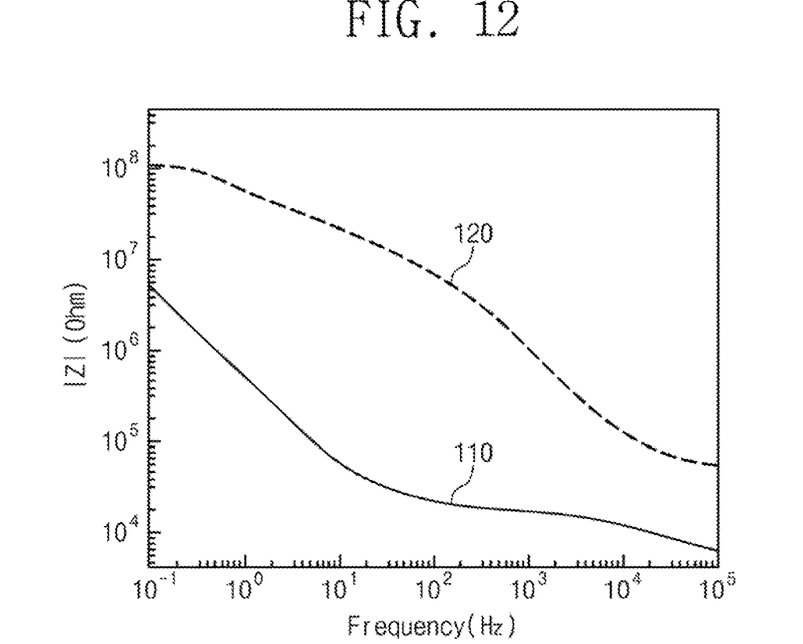
FIG. 12 is graphs for comparing the impedance of the neural electrode of the inventive concept and the impedance of a typical neural electrode without a metal oxide.

FIG. 12 compares and shows impedance 110 of the neural electrode 100 of the inventive concept shown in FIG. 9 and impedance 120 of a typical neural electrode without the metal oxide 60.

Referring to FIG. 12, the neural electrode 100 of the inventive concept may have the impedance 110 less than the impedance 120 of the typical neural electrode. Since the ITO nanowires 40 are configured to increase the surface area of the neural electrode 100, the impedance 110 of the neural electrode 100 may be less than the impedance 120 of the typical neural electrode. When the impedance 110 of the neural electrode 100 becomes small, noise of the neural electrode 100 may be reduced.

Figure 13:
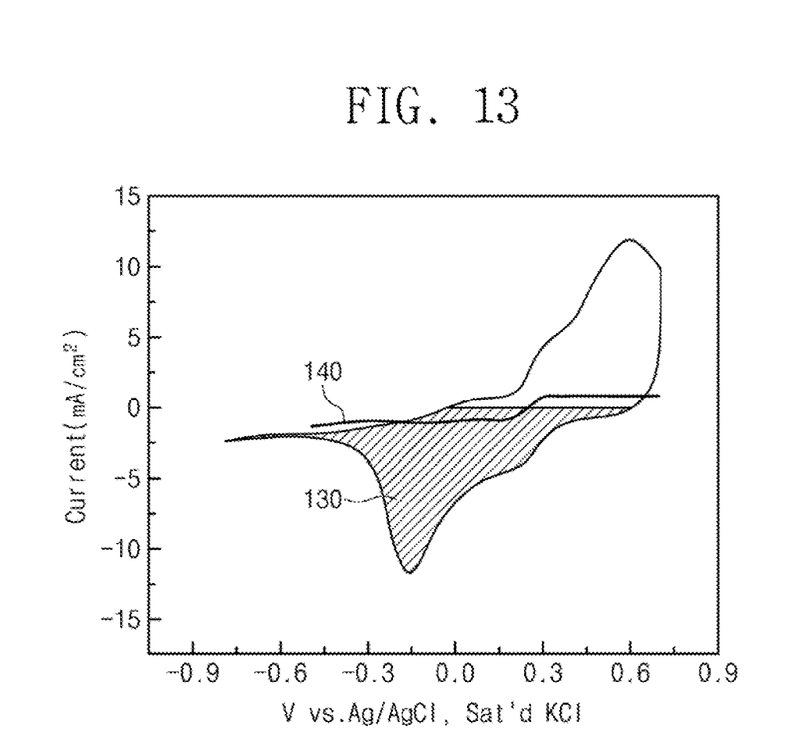
FIG. 13 is graphs for comparing the charge storage capacity of the neural electrode of FIG. 9 and the charge storage capacity of a typical neural electrode without a metal oxide.

FIG. 13 compares and shows charge storage capacity of the neural electrode 100 shown in FIG. 9 and charge storage capacity of a typical neural electrode without the metal oxide 60. Here, the horizontal axis represents voltage (ex, measured electrode relative to voltage (V vs Ag/AgCl, saturated KCl)) and the vertical axis represents current (mA/cm$^2$). The charge storage capacity (ex, CV, wherein C is capacitance and V is voltage) may be represented by an integral value (ex, area) at negative current.

Referring to FIG. 13, the neural electrode 100 of the inventive concept may have a charge storage capacity 130 greater than a charge storage capacity 140 of a typical neural electrode. When the charge storage capacity 130 of the neural electrode 100 increases, damage to a neuron may be reduced. On the contrary, when charge storage capacity 130 decreases, damage to the neuron may be increased.

Also, when the charge storage capacity 130 of the neural electrode 100 increases, charge injection limit may be increased. The charge injection limit may be defined as an amount of charge capable of moving to around an electrode without damaging the neuron. When the charge injection limit is increased, a margin of measured voltage of the neuron may increase.

As described above, the method for manufacturing a neural electrode according to an embodiment of the inventive concept may include forming ITO nanowires on an ITO electrode, and forming a metal oxide on the ITO nanowires. The ITO nanowires may increase surface area of an electrode to reduce impedance of the neural electrode, and the metal oxide may increase charge storage capacity of the neural electrode.

It will be understood by those skilled in the art that various changes in form and details may be made therein without departing from the spirit and scope of the inventive concept as defined in the appended claims. In addition, the embodiments disclosed in the present inventive concept are not intended to limit the technical spirit of the present inventive concept, and all technical ideas within the scope of the following claims and equivalents thereof should be construed as falling within the scope of the present inventive concept.

What is claimed is:

1. A method for manufacturing a neural electrode, comprising:
   forming an ITO electrode on a substrate;
   forming a passivation layer for exposing a portion of the ITO electrode;
   forming ITO nanowires on the ITO electrode; and
   forming a metal oxide on the ITO nanowires, the metal oxide including iridium oxide, the metal oxide being electrodeposited on the ITO nanowires,
   wherein electrodepositing the metal oxide comprises preparing an iridium oxide sol, and electrodepositing the iridium oxide by providing the substrate in the iridium oxide sol, wherein preparing the iridium oxide sol comprises mixing iridium chloride with water, the method further comprising: adding hydrogen peroxide to the water; adding oxalic acid to the water; and adding a pH adjusting agent to the water; and
   wherein electrodepositing the iridium oxide comprises a CV method.

2. The method of claim 1, wherein the pH adjusting agent includes potassium carbonate.

3. The method of claim 1, wherein the metal oxide is formed to have a thickness less than half the distance between the ITO nanowires.

4. The method of claim 1, wherein the passivation layer comprises silicon oxide.

5. The method of claim 1, wherein the substrate comprises transparent glass.

6. A method for manufacturing a neural electrode, the method comprising:
   forming an ITO electrode on a substrate;
   forming a passivation layer for exposing a portion of the ITO electrode;
   forming an ITO nanowire on the ITO electrode; and
   electrodepositing an iridium oxide on the ITO nanowire by providing the substrate in an iridium oxide sol, wherein electrodepositing the iridium oxide comprises a CV method, the method, further comprising: adding hydrogen peroxide to the water; adding oxalic acid to the water; and adding a pH adjusting agent to the water.

7. The method of claim 6, wherein the pH adjusting agent includes potassium carbonate.

8. The method of claim 6, wherein the iridium oxide is formed to have a thickness less than half the distance between the ITO nanowire.

9. The method of claim 6, wherein the passivation layer comprises silicon oxide.

10. The method of claim 6, wherein the substrate comprises transparent glass.

* * * * *